United States Patent [19]

Krämer et al.

[11] 3,972,891
[45] Aug. 3, 1976

[54] 1-PHENOXY-1-[HALO-1,2,4-TRIAZOLYL-(1)]-3,3-DIMETHYL-BUTAN-2-ONES

[75] Inventors: Wolfgang Krämer; Karl Heinz Büchel, both of Wuppertal; Wilhelm Brandes, Cologne; Paul-Ernst Frohberger, Leverkusen, all of Germany

[73] Assignee: Bayer Aktiengesellschaft, Leverkusen, Germany

[22] Filed: June 28, 1974

[21] Appl. No.: 484,355

[30] Foreign Application Priority Data
July 6, 1973 Germany............................ 2334352

[52] U.S. Cl............................ 260/308 R; 424/269
[51] Int. Cl.²........................................ C07D 249/08
[58] Field of Search .................................. 260/308 R

*Primary Examiner*—R. Gallagher

*Attorney, Agent, or Firm*—Burgess, Dinklage & Sprung

[57] ABSTRACT

1-Phenoxy-1-[halo-1,2,4-triazolyl-(1)]-3,3-dimethyl-butan-2-ones of the formula

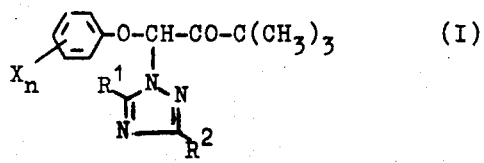

in which
 X is halogen, nitro, alkyl, haloalkyl or phenyl,
 $n$ is an integer from 0 to 5, and
 $R^1$ and $R^2$ each independently is halogen or hydrogen, provided at least one is halogen,
which possess fungicidal properties.

7 Claims, No Drawings

1-PHENOXY-1-[HALO-1,2,4-TRIAZOYL-(1)]-3,3-DIMETHYL-BUTAN-2-ONES

The present invention relates to and has for its objects the provision of particular new 1-phenoxy-1-[halo-1,2,4-triazolyl-(1)]-3,3-dimethyl-butan-2-ones, i.e. 1-(optionally substituted-phenoxy)-1-[3- and/or -5-halo-1,2,4-triazolyl-(1)]-3,3-dimethyl-butan-2-ones, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in German Published Specification DOS 1,795,249 that trityl-1,2,4-triazoles, for example triphenylmethyl-1,2,4-triazole (Compound A), display fungicidal properties. However, this activity is not always entirely satisfactory, especially if low amounts and low concentrations are used.

The present invention provides 1,2,4-triazole derivatives halogenated in the heterocyclic ring, of the general formula

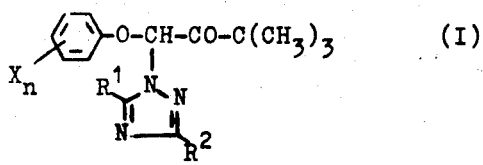

in which
X is halogen, nitro, alkyl, haloalkyl or phenyl,
n is an integer from 0 to 5, and
$R^1$ and $R^2$ each independently is halogen or hydrogen, provided at least one is halogen.

Preferably, X is chlorine, fluorine, bromine, nitro, phenyl, straight-chain or branched lower alkyl with 1 to 4 carbon atoms, especially methyl and tertiary butyl, of haloalkyl with 1 or 2 carbon atoms and 2 to 5 halogen atoms, especially fluorine; and n is an integer from 0 to 3.

When $R^1$ is halogen, it is preferably chlorine or bromine; when $R^2$ is halogen, it is preferably bromine or, when $R^1$ is hydrogen, preferably chlorine.

Surprisingly, the triazole derivatives according to the invention, of the formula (I), display a substantially greater fungicidal action than the trityl-1,2,4-triazoles known in the art, for example triphenylmethyl-1,2,4-triazole, which are chemically the nearest active compounds. The compounds according to the invention thus represent an enrichment of the art.

The invention also provides a process for the production of a 1,2,4-triazole derivative of the formula (I) in which
a. a haloether-ketone of the general formula

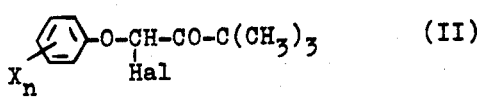

in which
X and n have the abovementioned meanings, and Hal is halogen, is reacted with a triazole of the general formula

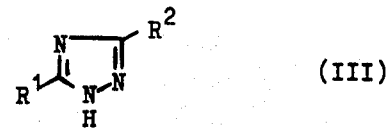

in which $R^1$ and $R^2$ have the abovementioned meanings, optionally in the presence of a diluent and optionally in the presence of an acid-binding agent; or (when $R^1$ represents bromine and $R^2$ represents hydrogen,
b. a triazole derivatve of the general formula

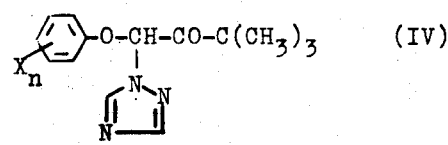

in which X and n have the abovementioned meanings, is reacted with bromosuccinimide, optionally in the presence of a solvent and optionally in the presence of a catalyst.

If 1-bromo-1-(4-chlorophenoxy)-3,3-dimethyl-butan-2-one and 3,5-dibromo-1,2,4-triazole are used as starting compounds, the course of the reaction in process variant (a) can be represented by the following formula scheme:

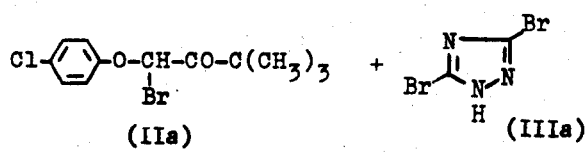

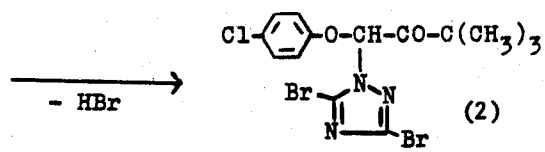

(V)

If 1-(4-nitrophenoxy)-1-[1,2,4-triazolyl-(1)]-3,3-dimethyl-butan-2-one and bromosuccinimide are used as starting compounds, the course of the reaction in process variant (b) can be represented by the following formula scheme:

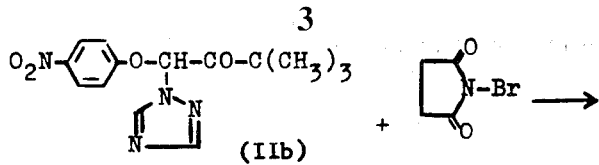

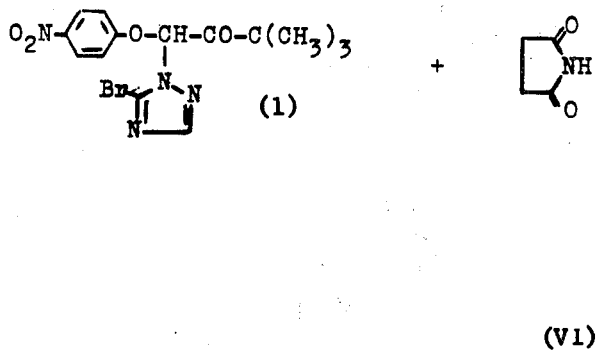

The formula (II) provides a general definition of the haloether-ketones which are used in process variant (a). In this formula, Hal preferably is chlorine or bromine.

Haloether-ketones of formula (II) are described in U.S. Patent Specification 3 812 142, the disclosure of which is incorporated herein by reference, and the compounds can be prepared according to the methods described therein.

The following are examples of these haloether-ketones:

1-bromo-1-(4-chlorophenoxy)-3,3-dimethyl-butan-2-one,
1-bromo-1-(2,4-dichlorophenoxy)-3,3-dimethyl-butan-2-one,
1-bromo-1-(2,4,5-trichlorophenoxy)-3,3-dimethyl-butan-2-one,
1-chloro-1-(2,3,4-trichlorophenoxy)-3,3-dimethyl-butan-2-one,
1-chloro-1-(2,3,6-trichlorophenoxy)-3,3-dimethyl-butan-2-one,
1-chloro-1-(2,3,5-trichlorophenoxy)-3,3-dimethyl-butan-2-one,
1-chloro-1-(3,4,5-trichlorophenoxy)-3,3-dimethyl-butan-2-one,
1-bromo-1-(3,4,6-trichlorophenoxy)-3,3-dimethyl-butan-2-one,
1-chloro-1-(3,4-dichlorophenoxy)-3,3-dimethyl-butan-2-one,
1-bromo-1-(2,6-dichlorophenoxy)-3,3-dimethyl-butan-2-one,
1-bromo-1-(2,5-dichlorophenoxy)-3,3-dimethyl-butan-2-one,
1-chloro-1-(3-chlorophenoxy)-3,3-dimethyl-butan-2-one,
1-chloro-1-(2-chlorophenoxy)-3,3-dimethyl-butan-2-one,
1-chloro-1-(4-chloro-2-methylphenoxy)-3,3-dimethyl-butan-2-one,
1-chloro-1-(4-nitrophenoxy)-3,3-dimethyl-butan-2-one,
1-chloro-1-(4-bromophenoxy)-3,3-dimethyl-butan-2-one,
1-chloro-1-(2-methylphenoxy)-3,3-dimethyl-butan-2-one,
1-chloro-1-(4-tertiary-butylphenoxy)-3,3-dimethyl-butan-2-one,
1-chloro-1-(4-diphenoxy)-3,3-dimethyl-butan-2-one,
1-chloro-1-(2-diphenoxy)-3,3-dimethyl-butan-2-one,
1-chloro-1-(3-trifluoromethylphenoxy)-3,3-dimethyl-butan-2-one,
1-chloro-1-(2-bromo-4-chlorophenoxy)-3,3-dimethyl-butan-2-one, and
1-chloro-1-(2-chloro-4-bromophenoxy)-3,3-dimethyl-butan-2-one.

The formula (III) provides a general definition of the triazoles which are used in process variant (a). These triazoles are described in Liebig's Annalen der Chemie 303 (1898), page 50–51 and Angewandte Chemie 77, 429 (1965) and can be prepared according to known processes.

The following are examples of these triazoles: 3,5-dibromo-1,2,4-triazole, 3-chloro-1,2,4-triazole and 3-bromo-1,2,4-triazole.

The triazole derivatives which are used in process variant (b) are generally defined by formula (IV). They can be prepared, as described in Application Ser. No. 318 963, filed Dec. 27, 1972, now pending, the disclosure of which is incorporated herein by reference, by reacting haloether-ketones of the formula (II) with 1,2,4-triazole, optionally in the presence of a diluent, at a temperature of 20° to 150°C, as described in Example 7 (a) hereinbelow, or by reacting hydroxyether-ketones of the formula

in which X and $n$ have the abovementioned meanings, with 1,2,4-triazole, optionally in the presence of a dehydrating agent and of a diluent, at a temperature of 100° to 230°C. Furthermore, triazole derivatives of the formula (IV) can also be obtained by reacting hydroxyether-ketones of the formula (VII) with thionyl-bis-1,2,4-triazole, optionally in the presence of a diluent, at a temperature of 0° to 120°C.

The following are examples of triazole derivatives of the formula (IV);

1-(4-fluorophenoxy)-1-[1,2,4-triazolyl-(1)]-3,3-dimethyl-butan-2-one,
1-(4-chlorophenoxy)-1-[1,2,4-triazolyl-(1)]-3,3-dimethyl-butan-2-one,
1-(4-bromophenoxy)-1-[1,2,4-triazolyl-(1)]-3,3-dimethyl-butan-2-one,
1-(4-nitrophenoxy)-1-[1,2,4-triazolyl-(1)]-3,3-dimethyl-butan-2-one,
1-(4-tertiary-butylphenoxy)-1-[1,2,4-triazolyl-(1)]-3,3-dimethyl-butan-2-one,
1-(4-trifluoromethylphenoxy)-1-[1,2,4-triazolyl-(1)]-3,3-dimethyl-butan-2-one,
1-(4-chloro-2-methylphenoxy)-1-[1,2,4-triazolyl-(1)]-3,3-dimethyl-butan-2-one,
1-(2,4-dichlorophenoxy)-1-[1,2,4-triazolyl-(1)]-3,3-dimethyl-butan-2-one, and 1-(3,4-dichlorophenoxy)-1-[1,2,4-triazolyl-(1)]-3,3,-dimethyl-butan-2-one.

If a diluent is used in process variant (a) it may be any polar organic solvent. Preferred ones include ketones such as acetone, diethyl ketone or methyl ethyl ketone, nitriles such as acetonitrile or propionitrile, alcohols such as ethanol or isopropanol and ethers such as tetrahydrofuran or dioxane.

The reaction in process variant (a) is desirably carried out in the presence of an acid-binding agent. Any inorganic or organic acid binder may be employed, such as alkali metal carbonates, for example sodium carbonate, or lower tertiary alkylamines, cycloalkylamines or aralkylamines, for example triethylamine, dimethylbenzylamine or dimethylcyclohexylamine.

The reaction temperature in process variant (a) can be varied over a wide range. In general, it is 20° to 150°C, preferably 80° to 120°C.

In carrying out process variant (a), preferably about 1 mole of the triazole of the formula (III) and about 1 mole of acid binder are employed per mole of the compound of the formula (II).

To isolate the product of the formula (I), the solvent may be distilled off in vacuo and the residue may be taken up by means of an organic solvent. This leaves the halide undissolved. The solution may be freed from the solvent in vacuo and the residue purified by recrystallization.

If a diluent is used in process variant (b) it may be any inert organic solvent. Preferred ones include aromatic hydrocarbons such as benzene, toluene or xylene, or chlorinated hydrocarbons such as chloroform or carbon tetrachloride.

It can be desirable to add a catalyst to initiate the reaction in process variant (b); preferably a peroxide, for example benzoyl peroxide, is used.

In process variant (b) the reaction temperature can be varied over a wide range; in general, it is 50° to 100°C, preferably 60° to 80°C. If a solvent is present, the reaction is suitably carried out at the boiling point of the particular solvent.

The reaction according to the invention is preferably carried out under normal pressure.

Preferably about 1 mole of N-bromosuccinimide and 0.001 to 0.5 mole of catalyst, for example a peroxide, are employed per mole of the compound of the formula (IV). Using amounts which exceed or fall below those mentioned does not produce any improvement in yield.

To isolate the active compounds according to the invention, the precipitate may be filtered off, the filtrate freed from the solvent in vacuo and the residue recrystallized from ligroin.

The active compounds according to the invention display a strong fungitoxic action. They do not harm crop plants in the concentrations required to combat fungi and have a low toxicity towards warm-blooded animals. For this reason, they are suitable for use as plant protection agents for combatting fungi. Fungitoxic agents in plant protection are employed for combatting Archimycetes, Phycomycetes, Ascomycetes, Basidiomycetes and Fungi Imperfecti.

The active compounds according to the invention have a very broad spectrum of action and can be used against parasitory fungi which attack above-ground parts of plants or attack plants through the soil, and against seed-borne pathogens.

They display a particularly good activity against parasitory fungi on above-ground parts of plants, such as species of Erysiphe, species of Podosphaera and species of Venturia and also against species of Piricularia and species of Pellicularia, for example against the pathogen of apple mildew (*Podosphaera leucotricha*), of cereal mildew (*Erysiphe graminis*) and of cucumber mildew (*Erysiphe cichoracearum*).

It should be emphasized particularly that the active compounds according to the invention not only display a protective action but are also curatively active, when used after contamination with the spores of the fungus. In addition, the systemic action of the compounds should be pointed out. Thus it proves possible to protect plants against fungal attack by supplying the active compound to the above-ground parts of the plant via the soil and the root. As plant protection agents, the compounds according to the invention can be used for the treatment of soil, for the treatment of seed and for the treatment of above-ground parts of plants.

The compounds according to the invention are well tolerated by plants. They only possess a low toxicity towards warm-blooded animals and, because of their low odor and their good toleration by human skin, they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. coventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, rodenticides, bactericides, nematocides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 1–95% by weight, and preferably 5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

When used as leaf fungicides, the active compound concentrations in the application forms can be varied within a wide range. They are generally 0.1 to 0.00001 per cent by weight, preferably 0.05 to 0.00001.

In the treatment of seed, amounts of active compound of 0.01 to 50 g per kilogram of seed, preferably 0.01 to 5 g, are generally required.

For the treatment of soil, amounts of active compound of 1 to 1,000 g per cubic meter of soil, preferably of 10 to 200 g, are generally required.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even 100% active substance alone, e.g. about 20–100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount of the particular active compound of the invention alone or together with a carrier vehicle as noted above. The instant formulations or compositions are applied in the usual manner, for instance by spraying, atomizing, vaporizing, scattering, dusting, watering squirting, sprinkling, pouring, fumigating, encrusting, dry dressing, moist dressing, wet dressing, slurry dressing, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Erysiphe test/protective

Solvent: 4.7 parts by weight of acetone

Emulsifier: 0.3 part by weight of alkylaryl polyglycol ether

Water: 95 parts by weight

The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23°–24°C and at a relative atmospheric humidity of about 75%.

After 12 days, the infection of the cucumber plants was determined as a percentage of the untreated but also inoculated control plants. 0% means no infection; 100% that the infection was exactly as great as in the case of the control plants.

The active compounds, the concentrations of the active compounds and the results can be seen from Table 1.

Table 1

Erysiphe test/protective

| Active compound | Infection in % of the infection of the untreated control at an active compound concentration of 0.00031% |
|---|---|
| 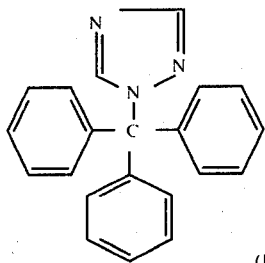<br>(known)<br>(A) | 41 |
| 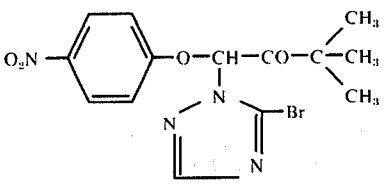<br>(I) | 15 |

Table 2

Podosphaera test/protective

| Active compound | Infection in % of the infection of the untreated control at an active compound concentration of 0.0012- 0.00062% 5% |
|---|---|
| 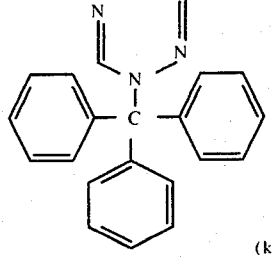<br>(known)<br>(A) | 52 |
| 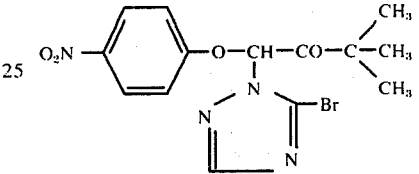<br>(I) | 11   32 |

EXAMPLE 2

Podosphaera test (powdery mildew of apples)/Protective

Solvent: 4.7 parts by weight of acetone

Emulsifier: 0.3 part by weight of alkylaryl polyglycol ether

Water: 95 parts by weight

The amount of active compound required for the desired concentration of the active compound in the spray liquid was mixed with the stated amount of solvent, and the concentrate was diluted with the stated amount of water which contained the stated additions.

Young apple seedlings in the 4 - 6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (*Podosphaera leucotricha*) and placed in a greenhouse at a temperature of 21° - 23°C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from Table 2.

EXAMPLE 3

Podosphaera test/systemic

Solvent: 4.7 parts by weight of acetone

Dispersing 0.3 part by weight of alkylaryl polyglycol Agent: ether

Water: 95 parts by weight

The amount of active compound required for the desired concentration of the active compound in the watering liquid was mixed with the stated amount of solvent and the concentrate was diluted with the stated amount of water which contained the stated additions.

Apple seedlings grown in standard soil, in the 3-4 leaf stage, were watered once within a week with 20 ml of the watering liquid, having the stated concentration of active compound, per 100 cc of soil.

After the treatment, the plants treated in this way were inoculated with conidia of *Podosphaera leucotricha* and placed in a greenhouse at a temperature of 21° – 23°C and a relative atmospheric humidity of approximately 70%. 10 days after the inoculation, the infection of the seedlings was determined as a percentage of the untreated but also inoculated control plants.

0% means no infection and 100% means that the infection was exactly as great as in the case of the control plants.

The active compounds, the concentrations of the active compounds and the results can be seen from Table 3.

Table 3

Podosphaera test/systemic

| Active compound | Infection in % of the infection of the untreated control at an active compound concentration of | |
|---|---|---|
| | 120 ppm | 25 ppm |
| 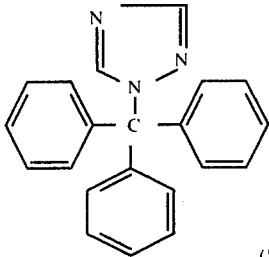 (known) (A) | 95 | |
| 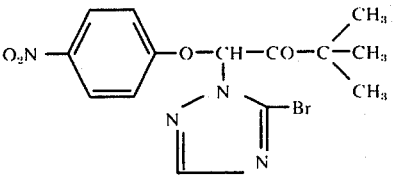 (1) | | 15 |

EXAMPLE 4

Shoot treatment test/powdery mildew of cereal/protective (leaf-destructive mycosis)

To produce a suitable preparation of active compound, 0.25 g part by weight of active compound was taken up in 25 parts by weight of dimethylformamide and 0.06 part by weight of alkylaryl polyglycol ether and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of Erysiphe graminis var. hordei.

After 6 days dwell time of the plants at a temperature of 21° – 22°C and 80 – 90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower was the degree of mildew infection.

The active compounds, active compound concentration, in the spray liquor and degrees of infection can be seen from Table 4.

Table 4

Shoot treatment test/powdery mildew of cereal/protective

| Active compound | Active compound concentration in the spray liquor in % by weight | Infection in % of the untreated control |
|---|---|---|
| untreated | | 100.0 |
| 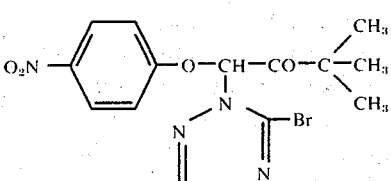 (1) | 0.001 | 0.00 |
| 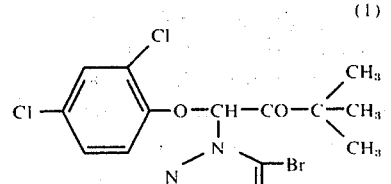 (8) | 0.01 | 0.00 |
| 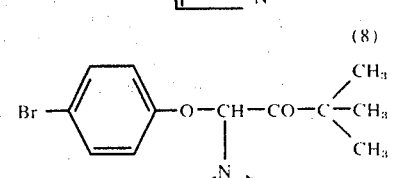 (4) | 0.01 | 8.75 |

Table 4-continued

Shoot treatment test/powdery mildew of cereal/protective

| Active compound | Active compound concentration in the spray liquor in % by weight | Infection in % of the untreated control |
|---|---|---|
| 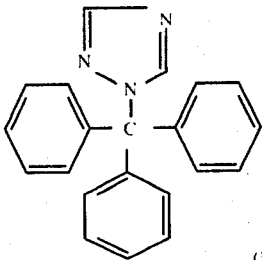 (known) (A) | 0.01<br>0.001 | 50.00<br>68.75 |

EXAMPLE 5

Shoot treatment test/powdery mildew of cereal/curative (leaf-destructive mycosis)

To produce a suitable preparation of active compound, 0.25 g part by weight of active compound was taken up in 25 parts by weight of dimethylformamide and 0.06 part by weight of alkylaryl polyglycol ether and 975 parts by weight of water were added. The concentrate was diluted with water to the desired final concentration of the spray liquor.

To test for curative activity, the procedure followed was analogous to that described in Example 4, but in inverse sequence. The treatment of the single-leaved young barley plants with the preparation of active compound took place 48 hours after the inoculation, when the infection was already manifest.

After 6 days' dwell time of the plants at a temperature of 21° – 22°C and 80 – 90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower was the degree of mildew infection.

The active compounds, active compound concentration, in the spray liquor and degrees of infection can be seen from Table 5.

Table 5

Shoot treatment test/powdery mildew of cereal/curative

| Active compounds | Active compound concentration in the spray liquor in % by weight | Infection in % of the untreated control |
|---|---|---|
| untreated | — | 100.00 |
| 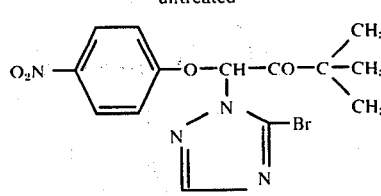 (1) | 0.001 | 11.25 |
| 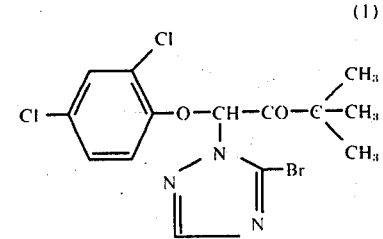 (8) | 0.001 | 16.25 |

Table 5-continued

Shoot treatment test/powdery mildew of cereal/curative

| Active compounds | Active compound concentration in the spray liquor in % by weight | Infection in % of the untreated control |
|---|---|---|
| 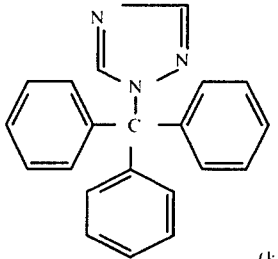 (known) (A) | 0.001<br>0.01 | 100.00<br>100.00 |

EXAMPLE 6

Powdery mildew of barley test (*Erysiphe graminis* var. *hordei*)/systemic (fungal disease of cereal shoots)

The active compounds were applied as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. hordei and grown on at 21° – 22°C and 80 – 90% relative atmospheric humidity and 16 hours' exposure to light. The typical mildew pustules formed on the leaves over the course of 6 days.

The degree of infection was expressed as a percentage of the infection of the untreated control plants. Thus, 0% denotes no infection and 100% denotes the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from Table 6.

Table 6

Powdery mildew of barley test (*Erysiphe graminis* var. *hordei*)/systemic

| Active compounds | Active compound concentration in the dressing, in % by weight | Amount of dressing used in g/kg of seed | Infection in % of the untreated control |
|---|---|---|---|
| without dressing | — | — | 100.00 |
| 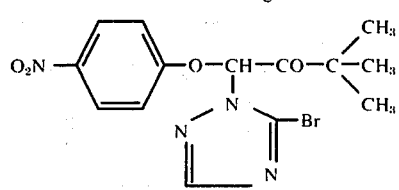 (1) | 25 | 2 | 0.00 |
| 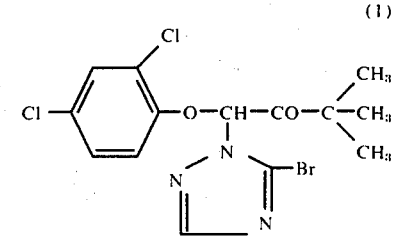 (8) | 25 | 2 | 0.00 |

Table 6-continued

Powdery mildew of barley test (*Erysiphe graminis* var. *hordei*)/systemic

| Active compounds | Active compound concentration in the dressing, in % by weight | Amount of dressing used in g/kg of seed | Infection in % of the untreated control |
|---|---|---|---|
| 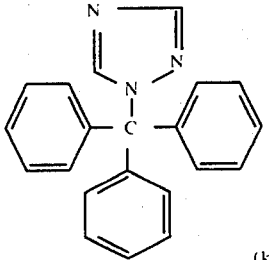 (known) | 25<br>25<br>25 | 2<br>4<br>10 | 100.00<br>100.00<br>88.75 |

EXAMPLE 7 a. The starting compound was prepared as follows:

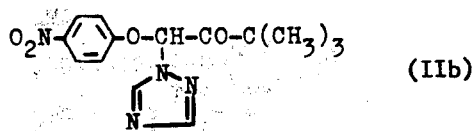
(IIb)

13.6 g (0.06 mole) of 1-chloro-1-(4-nitrophenoxy)-3,3-dimethyl-butan-2-one were added, with stirring, to a solution of 4 g (0.06 mole) of 1,2,4-triazole and 7.6 g (0.06 mole) of dimethylcyclohexylamine in 50 ml of isopropanol at room temperature. This produced initially a yellow-colored solution, the temperature rose to 26°C and after about 20 minutes a precipitate began to separate out. The reaction solution was stirred for 2 hours at room temperature and a further 2 hours at 40°C. After cooling to 0°C, the precipitate produced was filtered off and washed well with water. After drying, 11.2 g (74% of theory) of 1-(4-nitrophenoxy)-1-[1,2,4-triazolyl-(1)]-3,3-dimethyl-butan-2-one of melting point 136° – 140°C were obtained.

b) 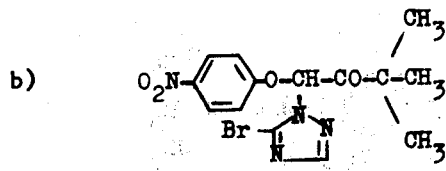 (1)

30.4 g (0.1 mole) of 1-(4-nitrophenoxy)-1-[1,2,4-triazolyl-(1)]-3,3-dimethyl-butan-2-one in 250 ml of carbon tetrachloride were boiled with 18 g (0.1 mole) of N-bromo-succinimide and 0.1 g (0.0041 mole) of benzoyl peroxide for 48 hours under reflux. The resulting precipitate was filtered off and rinsed with 50 ml of carbon tetrachloride, and the filtrate was freed from the solvent in vacuo.

The residue was recrystallized from ligroin/ethyl acetate. 24 g (63% of theory) of 1-(4-nitrophenoxy)-1-[5-bromo-1,2,4-triazolyl-(1)]-3,3-dimethyl-butan-2-one of melting point 107°–180°C were obtained.

EXAMPLE 8

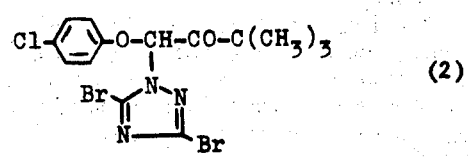
(2)

22.7 g (0.01 mole) of 3,5-dibromo-1,2,4-triazole and 30.4 g (0.01 mole) of 1-bromo-1-(4-chlorophenoxy)-3,3-dimethyl-butan-2-one were dissolved in 250 ml of anhydrous acetonitrile, 10.1 g (0.1 mole) of triethylamine were added dropwise and the mixture was heated for 6 hours under reflux. After distilling off the solvent in vacuo, the oily residue was taken up in 200 ml of ether and the insoluble triethyl-ammonium bromide was filtered off. The filtrate was freed from the solvent in vacuo. The residue was recrystallized from cyclohexane.

15 g (33% of theory) of 1-(4-chlorophenoxy)-1-[3,5-dibromo-1,2,4-triazolyl-(1)]-3,3-dimethyl-butan-2-one of melting point 92° were obtained.

The compounds in the table which follows were obtained analogously:

Table 7

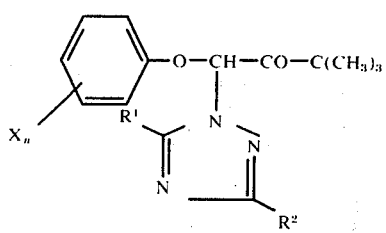

| Compound | X | n | R¹ | R² | Melting point, °C | Prepared according to process of Example |
|---|---|---|---|---|---|---|
| 3 | 4 -Cl | 1 | H | Cl | 128–130 | 8 |
| 4 | 4 -Br | 1 | Br | H | 75 | 7 |
| 5 | 4 -NO₂ | 1 | Br | Br | 144–146 | 8 |
| 6 | 4 -NO₂ | 1 | H | Cl | 136 | 8 |
| 7 | 2,4 -Cl₂ | 2 | Br | Br | 186–187 | 8 |
| 8 | 2,4 -Cl₂ | 2 | Br | H | 83–87 | 7 |
| 9 | 2,4 -Cl₂ | 2 | H | Cl | 132–134 | 8 |
| 10 | 4 -C₆H₅ | 1 | Br | Br | 108 | 8 |
| 11 | 4 -C₆H₅ | 1 | H | Cl | 124–127 | 8 |
| 12 | 4 -F | 1 | Br | H | boiling point 0.05 mm/137° C | 7 |
| 13 | 4 -Cl | 1 | Br | H | 69–71 | 7 |
| 14 | 2,4,5 -Cl₃ | 3 | Br | H | Oil (90% strength) | 7 |
| 15 | 4 -Br | 1 | H | Cl | 126 | 8 |
| 16 | 4 -Br | 1 | Br | Br | 99 | 8 |
| 17 | 4 -F | 1 | H | Cl | 71 | 8 |
| 18 | 4 -F | 1 | Br | Br | 96 | 8 |

Others compounds which can be similarly prepared include:

1-(pentachlorophenoxy)-1-[3,5-dichloro-1,2,4-triazolyl-(1)]-3,3-dimethyl-butan-2-one,
1-(3-trifluoromethylphenoxy)-1-[3-bromo-5-chloro-1,2,4-triazolyl-(1)]-3,3-dimethyl-butan-2-one,
1-(4-tertiary-butylphenoxy)-1-[5-bromo-1,2,4-triazolyl-(1)]-3,3-dimethyl-butan-2-one,
1-(2-bromo-4-chlorophenoxy)-1-[3-chloro-1,2,4-triazolyl-(1)]-3,3-dimethyl-butan-2-one,
and the like.

It will be appreciated that the instant specification and examples are set forth by way of illustration and not limitation, and that various modifications and changes may be made without departing from the spirit and scope of the present invention.

What is claimed is:

1. A 1-phenoxy-1-[halo-1,2,4-triazolyl-(1)]-3,3-dimethyl-butan-2-one of the formula

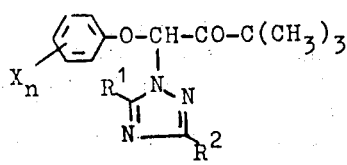

in which
X is chlorine, bromine, fluorine nitro, alkyl of 1 to 4 carbon atoms, haloalkyl.

2. A compound according to claim 1 in which R¹ is chlorine, bromine or hydrogen; and R² is hydrogen, bromine or, when R¹ is hydrogen, chlorine.

3. The compound according to claim 1 wherein such compound is 1-(4-nitrophenoxy)-1-[5-bromo-1,2,4-triazolyl-(1)]-3,3-dimethyl-butan-2-one of the formula

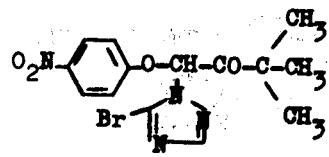

4. The compound according to claim 1 wherein such compound is 1-(4-chlorophenoxy)-1-[3,5-dibromo-1,2,4-triazolyl-(1)]-3,3-dimethyl-butan-2-one of the formula

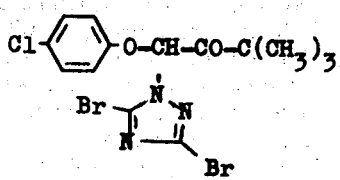

5. The compound according to claim 1 wherein such compound is 1-(4-bromophenoxy)-1-[5-bromo-1,2,4-triazolyl-(1)]-3,3-dimethyl-butan-2-one of the formula

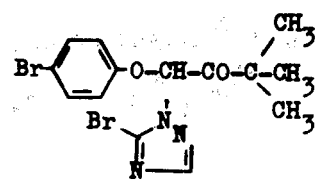

6. The compound according to claim 1 wherein such compound is 1-(2,4-dichlorophenoxy)-1-[5-bromo- 1,2,4-triazolyl-(1)]-3,3-dimethyl-butan-2-one of the formula
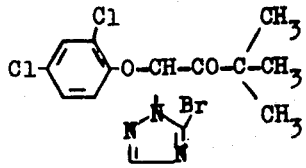
7. The compound according to claim 1 wherein such compound is 1-(4-chlorophenoxy)-1-[5-bromo-1,2,4-triazolyl-(1)]-3,3-dimethyl-butan-2-one of the formula
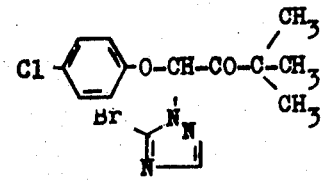
* * * * *

UNITED STATES PATENT AND TRADEMARK OFFICE
CERTIFICATE OF CORRECTION

PATENT NO. : 3,972,891
DATED : August 3, 1976
INVENTOR(S) : Kramer et al

It is certified that error appears in the above–identified patent and that said Letters Patent are hereby corrected as shown below:

Col. 2, line 17      cancel "derivatve" and substitute -- derivative --.

Col. 18, line 33      cancel "180" and substitute -- 108 --.

Col. 19, line 63      after "haloalkyl" insert -- of 1 to 2 carbon atoms and 2 to 5 halogen atoms or phenyl, n is an integer from 0 to 3, and $R^1$ and $R^2$ each independently is chlorine, bromine or hydrogen, provided at least one is chlorine or bromine --.

Signed and Sealed this

Fourteenth Day of June 1977

[SEAL]

Attest:

RUTH C. MASON
Attesting Officer

C. MARSHALL DANN
Commissioner of Patents and Trademarks